United States Patent
Weinstein et al.

(10) Patent No.: US 6,539,938 B2
(45) Date of Patent: Apr. 1, 2003

(54) MAXIMUM EXPIRATORY PRESSURE DEVICE

(75) Inventors: Lawrence A. Weinstein, Oneida, NY (US); Fredrick M. Richards, Clinton, NY (US); Deborah A. Laun, Syracuse, NY (US)

(73) Assignee: DHD Healthcare Corporation, Wampsville, NY (US)

( * ) Notice: Subject to any disclaimer, the term of this patent is extended or adjusted under 35 U.S.C. 154(b) by 105 days.

(21) Appl. No.: 09/738,756

(22) Filed: Dec. 15, 2000

(65) Prior Publication Data

US 2002/0073993 A1 Jun. 20, 2002

(51) Int. Cl.⁷ .............................................. A61M 15/00
(52) U.S. Cl. .................... 128/200.24; 600/538
(58) Field of Search ................. 128/200.24, 202.13, 128/202.21, 203.12, 203.23, 204.13, 205.24, 207.14, 207.16; 606/1; 600/529, 531, 532, 533, 538, 543

(56) References Cited

U.S. PATENT DOCUMENTS

| | | | |
|---|---|---|---|
| 3,298,362 A | 1/1967 | Lippitt, Jr. | |
| 3,511,228 A | 5/1970 | Lundgren | |
| 3,908,987 A | 9/1975 | Boehringer | |
| 4,211,240 A | 7/1980 | Gallagher | |
| 4,456,016 A | 6/1984 | Nowacki | |
| 4,601,465 A | 7/1986 | Roy | |
| 4,638,812 A | 1/1987 | Häkkinen | |
| 5,451,190 A | 9/1995 | Liardet | |
| 5,893,361 A | * 4/1999 | Hughes | 128/200.24 |
| 6,058,932 A | * 5/2000 | Hughes | 128/200.24 |
| 6,176,235 B1 | * 1/2001 | Benarrouch et al. | 128/205.12 |
| 6,340,025 B1 | * 1/2002 | Brunt | 128/204.18 |

* cited by examiner

Primary Examiner—Glenn K. Dawson
(74) Attorney, Agent, or Firm—August E. Roehrig, Jr.; Hancock & Estabrook, LLP

(57) ABSTRACT

An improved maximum expiratory pressure device and cough simulator including a flow tube having an integral mouthpiece at a patient input end, and a hinged door at an opposite or discharge end for sealing off the flow tube. The hinged door is held closed by a releasable trigger operable by the patient to release the door after pressure build up to simulate a cough. A foldable pressure monitoring port is provided to connect the maximum expiratory pressure device to a pressure gauge, if desired, for monitoring the expiratory pressure developed within the flow tube.

8 Claims, 1 Drawing Sheet

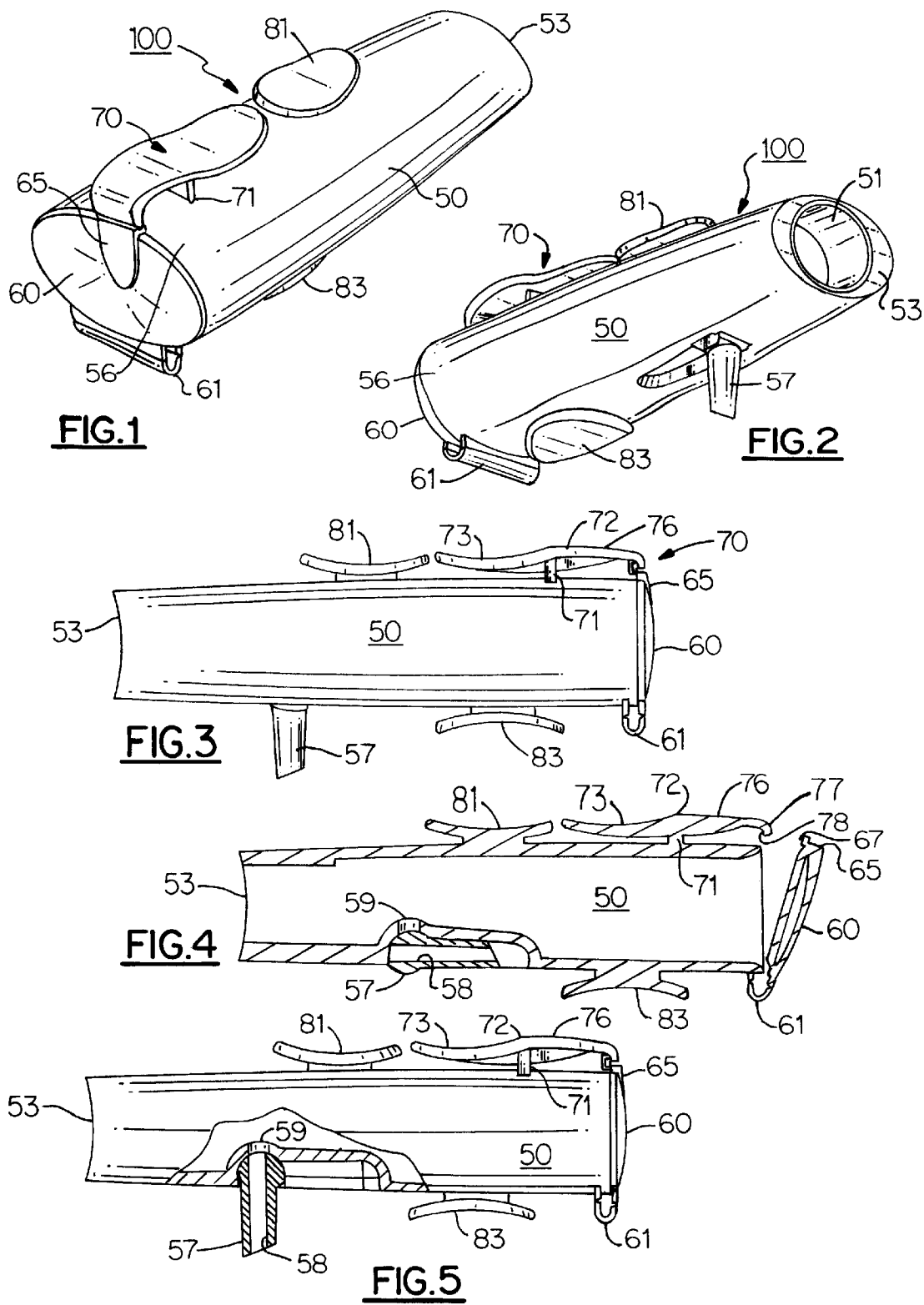

MAXIMUM EXPIRATORY PRESSURE DEVICE

BACKGROUND OF THE INVENTION

1. Field of the Invention

This invention relates in general to respiratory therapy and exercise devices and, in particular, to a single patient user, hand held, respiratory therapy and exercise device for assisting a user in obtaining maximal expiratory pressure and to simulate a cough. More specifically, but without restriction to the particular embodiment and/or use which is shown and described herein for purposes of illustration, this invention relates to a maximum expiratory pressure device which allows a user to read and record maximum expiratory pressure readings and to simulate a cough.

2. Description of Related Art

In many situations involving respiratory therapy and care, it is desirable that a patient cough to assist in the mobilization and clearance of secretions. However, getting a patient to cough is sometimes difficult, and frequently unsuccessful, requiring suctioning of secretions from the patient. The availability of a simple, inexpensive and reliable device to permit a patient to exert maximal expiratory pressure would improve respiratory muscle strength, alleviate the symptoms of neuromuscular diseases that involve the diaphragm, and permit a health care provider to monitor a patient on mechanical ventilation. The availability of such a device for simulating a cough would assist a patient in being able to mobilize and clear secretions, thereby avoiding suctioning procedures.

The present invention provides such a device through the use of a flow tube having an integral mouthpiece at a patient input end, and a hinged door at an opposite or discharge end for sealing off the flow tube. The hinged door is held closed by a releasable trigger operable by the patient to release the door after pressure build up to simulate a cough. A foldable pressure monitoring port is provided to connect the maximum expiratory pressure device to a pressure gauge, if desired, for monitoring the expiratory pressure developed within the flow tube.

SUMMARY OF THE INVENTION

It is an object of this invention to improve maximum expiratory pressure respiratory therapy and care devices.

Another object of this invention is to improve respiratory therapy and care cough simulation devices.

Still another object of this invention is to provide a single patient user, hand held, respiratory therapy and exercise device for assisting a user in obtaining maximal expiratory pressure and to simulate a cough.

These and other objects are attained in accordance with the present invention wherein there is provided an improved maximum expiratory pressure and cough simulation device including a flow tube having an integral mouthpiece at a patient input end, and a hinged door at an opposite or discharge end for sealing off the flow tube. The hinged door is held closed by a releasable trigger operable by the patient to release the door after pressure build up for determining maximum expiratory air pressure or to simulate a cough. A foldable pressure monitoring port is provided to connect the maximum expiratory pressure device to a pressure gauge, if desired, for monitoring the expiratory pressure developed within the flow tube.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein:

FIG. 1 is a frontal perspective view of the upper portion of the improved maximum expiratory pressure and cough simulation respiratory therapy and care device of our invention;

FIG. 2 is a rear perspective view of the bottom portion of the improved maximum expiratory pressure and cough simulation respiratory therapy and care device of our invention to better illustrate the foldable pressure port illustrated in an extended position;

FIG. 3 is a side elevational view of our invention with the door held closed to occlude the passage of expiratory air from the flow tube;

FIG. 4 is a longitudinal cross sectional view of our device as illustrated in FIG. 3, taken along lines 4—4, with the closure door illustrated in an open or released position and the pressure port retracted; and FIG. 5 is a side elevational view of our device as illustrated in FIG. 3, with portions broken away to better illustrate the internal structure of the foldable pressure port when in an extended position for connection to a pressure gauge.

This and additional embodiments of the invention may now be better understood by referring to the following detailed description of the invention wherein the illustrated embodiment is described.

DETAILED DESCRIPTION OF THE INVENTION

Throughout this description, the preferred embodiment and examples shown should be considered as exemplars, rather than limitations on the apparatus and methods of the present invention.

Referring now to the drawings, there is shown in FIGS. 1 and 2 a maximum expiratory pressure device and cough simulator 100 which includes a cylindrical flow tube 50, having an integral mouthpiece 51 at a patient input end 53 through which a patient inhales and exhales, and a discharge end 56 which is selectively closed by a closure or door 60 hinged to the flow tube 50 by a hinge 61 for sealing the open discharge end 56 of the flow tube 50. The integral mouthpiece 51 has an internal diameter sized to receive a standard 15 millimeter ID fitting for receiving an endotracheal tube or other respiratory connector (not shown) if desired.

An integral pressure port 57 is carried within the flow tube 50, and may be folded into or out from the body of the flow tube 50 as illustrated in these figures and in more detail in FIGS. 4 and 5, respectively. When the pressure port 57 is folded within the body of the flow tube 50, as illustrated in FIG. 4, an opening 59 formed in the flow tube is closed by the pressure port 57, blocking passage of air therethrough and through a passage 58 in the pressure port. When the pressure port 57 is extended out from the body of the flow tube 50, as illustrated in FIG. 5, the passage 58 in the pressure port 57 within the flow tube is coupled through the opening 59 in the flow tube 50 so that the pressure port 57 may be connected, as by tubing, to a suitable pressure gauge to monitor expiratory pressure during therapy. The pressure monitoring port 57 is adapted to be connected to standard flexible tubing for connection to a pressure-monitoring device, such as an aneroid gauge (not shown).

As shown in the drawings, the open discharge end 56 of the flow tube 50 has a closure or door 60 for sealing the open end and thereby occluding air flow through the flow tube. The door 60 is hinged (61) to the flow tube 50, and is maintained in the closed position allowing a patient to generate a maximum positive expiratory pressure when exhaling into the flow tube 50 through the mouthpiece 51. Through the use of the pressure port 57, in conjunction with a pressure gauge, a patient's maximum expiratory pressure readings may thereby be obtained and recorded. An upper finger pad 81 and lower finger pad 83 are carried by the flow tube 50 for receiving the index finger and thumb, respectively, of a user's hand to stabilize the device when in use.

When the door 60 is opened while a patient is exhaling, and generating a positive expiratory pressure, illustrated in FIG. 4, the opening of the door 60 causes a rapid reduction in pressure along with a high expiratory flow rate. This sudden reduction of expiratory pressure and rapid discharge of expiratory air simulates a cough, the opening of a closed glottis against high airway pressure, to assist in the mobilization and clearance of secretions. To this end, the door 60 is formed with a latch 65 carried thereon at a position opposite from the hinge connection 61. The latch 65 includes an undercut or stepped lip 67 extending radially outward from the door 60 to a position, when the door 60 is closed, wherein the latch 65 extends outwardly beyond the body of the flow tube 50.

To hold the door 60 sealed against the open discharge end 56 of the flow tube 50, occluding the flow of expiratory air therethrough, a patient-operable trigger 70 is carried on the body of the flow tube 50. The trigger 70 is secured to the flow tube 50 through a pivot connection 71 formed at the midpoint of a lever arm 72, thereby enabling the lever arm to pivot vertically up and down about the pivot connection 71. A first end 73 of the lever arm 72 is positioned towards the patient input end 53, and is formed as a trigger pad to receive a patient's finger for controlling the release of the trigger 70, and the opening of the door 60. The opposite end 76 of the lever arm 72 is positioned towards the flow tube discharge end 56, and is formed as a release 77 to engage the lip portion 67 of the door 60. The release portion 77 includes an undercut or stepped lip 78 for engaging the lip 67 of the door 60 to hold the door 60 sealed against the open discharge end 56 of the flow tube 50. In this manner the air flow through the flow tube 50 is occluded until the trigger pad 73 is depressed, raising the release 77 to move the lip 78 out from engagement with the lip 67 on the door 60.

When the door 60 is released, the expiratory pressure within the flow tube 50 will cause a rapid reduction in pressure, along with a high expiratory flow rate, which simulates a cough, the opening of a closed glottis against high airway pressures to assist in the mobilization and clearance of secretions.

While this invention has been described in the specification and illustrated in the drawings with reference to a preferred embodiments, the structure of which has been disclosed herein, it will be understood by those skilled in the art to which this invention pertains that various changes may be made, and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims:

It is claimed:

1. A respiratory therapy device for applying a maximum expiratory pressure to the respiratory system of a user and simulating a cough, comprising:

a housing having an opening therethrough through which a user may exhale expiratory air, said housing having a proximal end for engagement by a user and through which the user exhales into the housing, said housing having a distal end open to ambient air and through which user exhaled expiratory air may be passed from the housing, a closure positioned adjacent said distal end of said housing and movable between a first position sealing said open distal end and occluding the flow of expiratory air therethrough, and a second position permitting the flow of expiratory air therethrough, and a user actuated trigger for releasing said closure from said first position to said second position during exhalation thereby simulating the opening of a closed glottis against high airway pressures.

2. The respiratory therapy device of claim 1 further including a pressure port in fluid communication with said housing for coupling the expiratory pressure within said housing to a pressure gauge.

3. The respiratory therapy device of claim 2 wherein said pressure port is retractable within said housing to terminate the fluid communication with said housing.

4. The respiratory therapy device of claim 1 further including support pads engagable by a user to support said device when in use.

5. The respiratory therapy device of claim 1 wherein said proximal end of said housing is adapted to receive an endotracheal tube.

6. The respiratory therapy device of claim 1 wherein said closure is secured to said housing adjacent to said distal end thereof.

7. The respiratory therapy device of claim 6 wherein said closure includes a latch having a stepped lip extending radially outward from said closure to a position outwardly beyond said housing for selectively closing said open discharge end of said housing.

8. The respiratory therapy device of claim 7 wherein said user actuated trigger includes a lip portion for engaging said lip of said latch to hold said closure sealed against said open discharge end of said housing to occlude the flow of expiratory air therethrough until said user actuated trigger is released thereby simulating the opening of a closed glottis against high airway pressures.

\* \* \* \* \*